United States Patent [19]

Zauner

[11] 4,293,958

[45] Oct. 13, 1981

[54] HEAD GEAR

[76] Inventor: Christian W. Zauner, 4139 SW. Archer Rd., Gainesville, Fla. 32608

[21] Appl. No.: 153,048

[22] Filed: May 27, 1980

[51] Int. Cl.$^3$ ............................................. A61F 9/04
[52] U.S. Cl. ....................................... 2/12; 2/209.1; 2/DIG. 11
[58] Field of Search .................... 2/12, 171, 195, 196, 2/209.1, DIG. 11

[56] References Cited

U.S. PATENT DOCUMENTS

| | | | |
|---|---|---|---|
| 1,506,815 | 9/1924 | Cormay | 2/195 |
| 2,019,028 | 10/1935 | Sternberg | 2/12 |
| 2,736,035 | 2/1956 | Spreiregen | 2/195 |
| 3,344,437 | 10/1967 | Greene | 2/195 |

*Primary Examiner*—Peter P. Nerbun
*Attorney, Agent, or Firm*—Arthur W. Fisher, III

[57] ABSTRACT

An article of apparel specifically designed to be worn on or about the head of a wearer and comprising in essence a combination head band and shade producing element extending outwardly therefrom. A support band is specifically configured to be disposed in surrounding relation to the upper portion of the wearer's head in somewhat conventional fashion. A visor is at least partially defined by a flexible material pouch specifically configured to have mounted therein a visor support element so as to provide outward extension of the visor relative to the face or other predetermined portion of the wearer's head wherein the visor support element can be readily removed from the pouch to allow washing of the entire article of apparel or alternately for folding over of the visor portion about itself in surrounding relation to the support band so as to essentially function as a band used primarily to absorb perspiration from the head of the wearer.

8 Claims, 4 Drawing Figures

HEAD GEAR

BACKGROUND OF THE INVENTION

1. Field of the Invention

This invention relates to an article of apparel of the type designed to be worn primarily in surrounding relation to the head of the wearer and further structured so as to offer shade to the face or other portion of the head through provision of a visor structure wherein the entire article is capable of being washed and the visor portion is capable of being displaced out of forward extension from the support band so as to change the overall configuration of the article of apparel.

2. Description of Prior Art

Articles of apparel specifically designed to be worn on or about the head and broadly classified as head gear have been popular for numerous years in all cultures and environments. In modern times certain head gear has been specifically designed for certain application. Such head gear is commonly worn for protection both from the cold and sun, first in offering warmth in covering major portions of the head and second in offering shade from the sometimes damaging rays of the sun.

Since modern society has increasing amounts of leisure time in which to follow activities not specifically related to work, a greater portion of this leisure time is spent outdoors. Accordingly various recreational activities are made easier and/or more comfortable through the use of various types of head gear which are specifically designed to accomplish specific function such as providing shade, absorbing perspiration, and/or generally increasing the cooling effect by blocking the head from direct exposure to the sun.

Accordingly, the use of sun visors and/or perspiration or "sweat" bands are now in substantial demand to the consuming public. Generally, such head gear is normally designed to include a permanently attached visor portion secured in nonremovable fashion to some type of support structure which mounts or secures the head gear to the head of the wearer. Alternately numerous types of sweat bands are available on the market which generally do not offer shade to portions of the head. These sweat bands are generally made from a moisture absorbent material and fit snuggly about the head so as to hold down portions of the hair as well as preventing perspiration passing from the forehead into the eyes or lower portions of the face of the wearer.

While prior art bands are commonly made of cloth like material and readily capable of being washed, numerous types of visor type head gear are not capable of such washing. In addition head gear, when exposed to the outdoors is generally subjected to somewhat harsh environment both from the standpoint of absorbing perspiration from the head wearer and being exposed to the elements. Accordingly, such visor structure frequently become soiled and cleaning of these visor structures in an effective manner becomes a problem.

It is readily apparent that there are certain activities and/or applications where head gear should be somewhat more versatile than numerous articles presently available to the consuming public. Such versatility should include the provision of removing the visor portion and disposition of this portion in some location capable of altering the overall configuration of the article of apparel from a visor type head gear to a head band or sweat band. Also the structure of the preferred head gear should be capable of being washed and reused without altering, in a harmful fashion, the overall appearance or structure of the head gear after such washing.

Finally, such an article of apparel or head gear should be structured so as to maintain a substantially long operable life and should be available to the general public at a reasonable price while at the same time incorporating all of the desired features not normally present in many of the articles now presently commercially available.

SUMMARY OF THE INVENTION

This invention relates to an article of apparel or head gear structure specifically designed to be disposed in surrounding relation to the head of the wearer and primarily worn during times of recreation or otherwise exposure to the elements and specifically the sun's rays or the like. In addition, and as will be explained in greater detail hereinafter, the head gear of the subject invention is designed to be washable after use and when soiled through removal of specific support portions thereof. Also removal of the aforementioned support portions also increases the overall versatility of the subject invention by allowing changing of the configuration of the structure and allowing its use without the apparent provision of a shade producing element or visor.

The structure of the subject invention comprises a support means in the form of a band means specifically disposed to have a substantially circular configuration so as to fit in surrounding relation to predetermined portions of the head of the wearer in a somewhat conventional fashion. This band means may be formed from a flexible material so as to add to the comfort of the user and further may be formed from a cloth material which is a moisture absorbent. In this embodiment, such moisture absorbent cloth material can serve as a "sweat band" which will be explained in greater detail hereinafter. Another structural feature of the present invention comprises the provision of a visor means. The visor means includes a pouch means having one edge portion permanently secured to the band means and having the exterior leading edge disposable outwardly from the band means so as to allow the outward extension of the visor means.

This outward extension is provided through the use of a visor support means in the form of a "stiffening" or other semi-rigid support element. This visor support means may have a specific configuration generally corresponding to that of the interior of the pouch. In addition the overall dimension of the visor support means must be such as to readily fit on the interior of the pouch and yet allow the easy removal of the visor support means from the interior of the pouch when it is intended or desired to wash the article of apparel or otherwise change its configuration.

The pouch means is further defined by at least one opening located substantially adjacent to the junction in between the visor means and the band means. The dimension of the single opening of the pouch, at its widest point, is somewhat greater than the greatest transverse dimension of the visor support means. Again, this allows ready insertion and removal of the visor support means from the interior of the pouch as desired.

In a preferred embodiment the leading edge of the visor support means substantially corresponds to a leading edge portion of the pouch so as to provide the pouch with the desired shape of configuration when the visor support means is supported therein.

The visor means including the pouch structure may also be formed of a flexible, cloth material which itself may be substantially moisture absorbent. Accordingly, upon removal of the visor support means from the interior of the pouch, the entire pouch structure may be folded over upon itself in substantially surrounding relation to a predetermined length of the band means. This effectively allows disposal of the article of apparel into a head band or sweat band configuration.

In addition, when the visor support means is removed from the pouch and further providing that the entire article is formed from a cloth of like flexible material, the article may be washed and readily cleaned in an effective manner without changing the shape or the configuration or otherwise harmfully effecting the appearance of the visor means after washing.

Other structural features of the present invention includes the provision of a biasing means connected or otherwise attached directly to the head band. This biasing means may take the form of an elastic material portion connected directly to the head band. When so installed the biasing means allows expansion and/or contraction of the circumferential dimension of the head band. This in turn allows a relatively snug but comfortable fit of the band means when it is disposed in surrounding relation to and in contact with the head of the wearer of article. In addition an adjustable connector is connected to the biasing means to further facilitate enlarging of the sweat band portion to fit about the head.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature and objects of the invention, reference should be had to the following detailed description taken in connection with the accompanying drawings in which.

DETAILED DESCRIPTION OF THE PREFERRED EMBODIMENT

Figure 1:
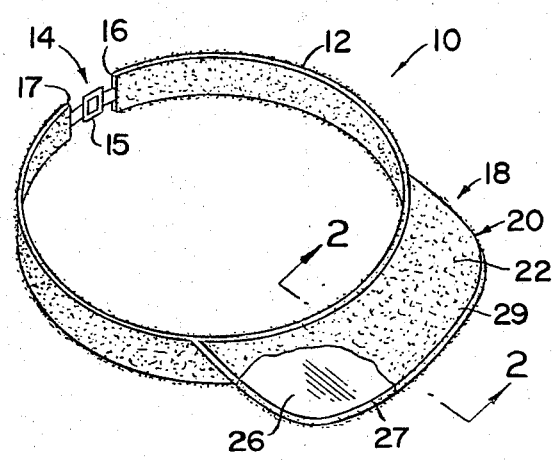
FIG. 1 is a top perspective view in partial cutaway showing the interior of the visor assembly.
Figure 3:
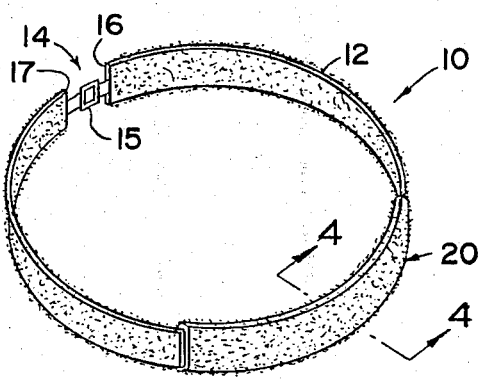
FIG. 3 is a top perspective view of the structure of the present invention with the visor means in folded over relation to itself.
Figure 2:
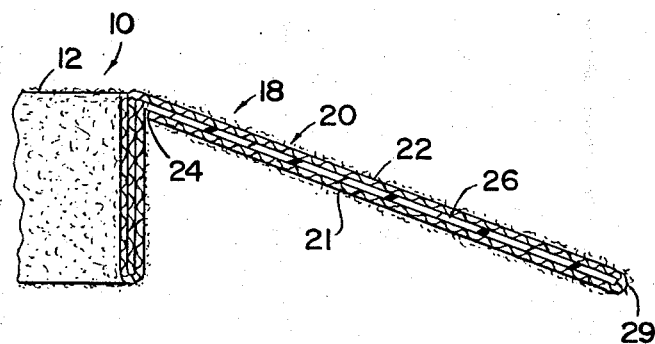
FIG. 2 is a sectional view in partial cutaway showing structural details of the visor support means and visor means.

The present invention is directed to an article of apparel as best shown in FIGS. 1 and 3 comprising head gear generally indicated as 10 designed to be worn snuggly but comfortably in surrounding relation to an uper portion of the head. The head gear 10 comprises a band means 12 comprising a substantially annular or circular configuration. A biasing means 14 comprises a portion of elastic material 15 extending between spaced apart end portion 16 of the band means 12. The elastic material 15 is such as to allow some expansion of the circumference dimension of the band means 12 so as to allow it to fit on and surround the head of the wearer. The head gear 10 further comprises a visor means generally indicated as 18 (FIGS. 1 and 2). The visor means includes a pouch means 20 including a top or upper surface 21 and an under or lower surface 22.

The pouch means 20 further comprises an opening aperture as at 24 disposed or formed contiguous the lower surface 22 substantially at the junction of the lower surface 22 with the band means 12 as best shown in FIGS. 1 and 2.

It is important to note that both the band means 12 and the pouch means or visor means 20 and 18 generally respectively are formed from a cloth material capable of being washed and specifically capable of being greatly flexible. A visor support means 26 comprises a support element having an overall configuration substantially similar to the interior of the pouch means 20. This support element is formed from a semi-rigid material which is capable of a certain amount of flexure but at the same time sufficiently rigid to maintain the visor means in a substantially outwardly projecting position relative to the band means 12. Ideally, the support means 26 is designed to be fit on the interior of the pouch means so as to define the outward projection of the visor means. In such outwardly projecting position the visor means offer shade and general protection from the elements to the face of the wearer. Accordingly the visor means is disposed in over hanging and outwardly projecting relation to the eyes and/or face portion of the head of the wearer.

Provision of the entrance aperture 24 of the pouch means 20 is provided to allow ready placement and removal of the visor support means or support element 26 from the interior of the pouch means 20.

As set forth above, when the support element 26 is maintained on the interior of the pouch means as shown in FIG. 2 the result is an outwardly extending projection of the visor means 18 as best shown in FIG. 2. However, the support element, is removable from the interior of the pouch means and when so removed the entire head gear 10 may be washed. The removability of the support element 26 also lends greater versatility of the overall head gear 10. This versatility is further evidenced in the ability to fold over the visor means 18 about itself and about a predetermined length of the band means 12 as shown in FIGS. 3 and 4.

Figure 4:
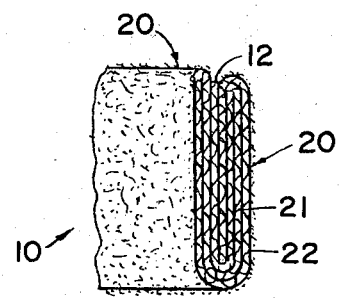
FIG. 4 is a sectional view taken along line 4-4 of FIG. 3 Similar reference characters refer to similar parts throughout the several views of the drawings.

As best shown in FIGS. 3 and 4 the folded over orientation of the pouch means, about the predetermined length of the band means 12 allows an additional adaptability of the head structure 10 so as to essentially be worn in a configuration similar to a headband or "sweat band." Such general apparel is known in the art.

Due to the fact that the material from which both the visor means 18 and the band means 12 are formed in cloth or the like, such material can further be specified as being moisture absorbent. This characteristic allows perspiration forming about the head of the wearer to be absorbed by the band means as well as the folded over visor means and/or pouch means 18 and 20 respectively. Further with regard to the relative structure and configurations of the support element 26 and the pouch means 20, the peripheral edge of the support element as at 27 is substantially similar in both dimension and configured to the leading peripheral edge portion 29 of the pouch means. This insures a snug and trim fit of the visor support element 26 on the interior of the pouch means 20 allowing the full extension of the pouch means 20 in the manner indicated in FIG. 2. As demonstrated in FIG. 1 the general overall configuration of the support element 26 is substantially equivalent to but somewhat lesser than the overall configuration and dimension of the interior of the pouch means 20. Along these lines the equivalent but specifically somewhat lesser than the dimension of the aperture 24 so as to allow easy insertion of the support element 26 in the interior of the pouch means 20 through such entrance aperture 24.

In addition, an adjustable connector 40 is interconnected to the biasing means and is so disposed to allow the positioning of the length of biasing means 14 to fit about the head of the wearer.

It will thus be seen that the objects set forth above, among those made apparent from the preceding description are efficiently attained and since certain changes may be made in the above construction without departing from the scope of the invention, it is intended that all matter contained in the above description or shown in the accompanying drawing shall be interpreted as illustrative and not in a limiting sense.

It is also to be understood that the following claims are intended to cover all of the generic and specific features of the invention herein described, and all statements of the scope of the inveniton which, as a matter of language, might be said to fall therebetween.

Now that the invention has been described,
What is claimed is:

1. An article of apparel of the type to be worn on the head, said article comprising: support means including at least in part a band means, said band means having a substantially circular configuration and disposable in surrounding relation to a portion of the head of the wearer; visor means attached to said support means and including a pouch means, a substantially flat visor support means mountable on the interior of said pouch means, said pouch means disposed relative to said band means to extend outwardly therefrom when said visor support means is mounted on the interior of said pouch means, whereby said visor means is positioned to offer shade to a predetermined portion of the wearer's head, said pouch means and said band means are formed from a substantially flexible moisture absorbent material, said pouch means being disposed in a folded over relation to itself and in at least partially surrounding relation to a predetermined length of said band means, upon absence of said visor support means from the interior of said pouch means, said predetermined length substantially equal to the transverse dimension of said visor means, whereby said band means is disposed so as to substantially function as perspiration absorbing band when mounted on the head of a wearer.

2. An article of apparel as in claim 1 wherein both said band means and said visor means are formed form a cloth material, said cloth material capable of being washed.

3. An article of apparel as in claim 1 further comprising biasing means connected to said band means along a portion of the length thereof and disposed to allow expansion and contraction of the circumferential dimension of said band means when said band means is oriented for placement and removal on the head of the wearer of said article of apparel.

4. An article of apparel as in claim 1 wherein said visor support means is substantially correspondingly dimensioned relative to said interior of said pouch means and is removably positioned on the interior of said pouch means, whereby said visor support means is removable from said pouch means for washing of said article of apparel.

5. An article of apparel as in claim 4 wherein said visor support means if formed from a material having a sufficient stiffness to dispose said visor means in substantially outwardly extending relation to said band means when said visor support means is disposed on the interior of said pouch means.

6. An article of apparel as in claim 1 wherein said pouch means has a single opening disposed substantially adjacent the junction of said visor means and said band means, said opening having a dimension at its widest point somewhat greater than the greatest transverse dimension of said visor support means, whereby said visor support means is disposable on the interior of said pouch means and maintained therein during use of said article of apparel.

7. An article of apparel as in claim 4 wherein said visor support means comprises a leading peripheral edge portion substantially equivalent to at least a major portion of the length of the leading edge of said pouch means.

8. An article of apparel as in claim 7 wherein the longitudinal dimension of said visor support means is substantially equivalent to the lesser dimension of said visor means extending from the leading edge of said visor means to approximately the junction of said visor means and said band means.

* * * * *